United States Patent [19]

Parker

[11] 4,286,105
[45] Aug. 25, 1981

[54] PROCESS FOR THE PREPARATION OF ANTIOXIDANT AMIDES

[75] Inventor: Dane K. Parker, Massillon, Ohio

[73] Assignee: The Goodyear Tire & Rubber Company, Akron, Ohio

[21] Appl. No.: 92,820

[22] Filed: Nov. 9, 1979

[51] Int. Cl.³ .......................................... C07C 102/04
[52] U.S. Cl. .................................. 564/205; 564/138; 564/139; 564/141
[58] Field of Search .......... 260/561 N, 562 A, 562 R; 564/138, 139, 141, 205

[56] References Cited

U.S. PATENT DOCUMENTS

| | | | |
|---|---|---|---|
| 2,628,977 | 2/1953 | Grigsby | 260/561 N |
| 3,151,158 | 9/1964 | Schmitt et al. | 260/562 A |
| 3,660,486 | 5/1972 | Thiele | 260/562 A X |
| 3,907,893 | 9/1975 | Parker | 260/561 N X |
| 3,945,970 | 3/1976 | Spoerke | 260/562 R X |
| 4,036,633 | 7/1977 | Perronnet et al. | 260/562 A X |
| 4,039,316 | 8/1977 | Perronnet et al. | 260/562 A X |

*Primary Examiner*—Arthur P. Demers
*Attorney, Agent, or Firm*—D. O. Nickey

[57] ABSTRACT

An inexpensive and nonhazardous process for the preparation of an amide wherein an organic acid reacting with an aryl amine to form an intermediate hydroxy aryl amide and then dehydrating the hydroxy aryl amide to form a $\alpha, \beta$ unsaturated amide.

7 Claims, No Drawings

PROCESS FOR THE PREPARATION OF ANTIOXIDANT AMIDES

TECHNICAL FIELD

This invention relates to a process for preparing aryl amides. More particularly, it relates to a new process for preparing a hydroxy amide, such as N-(4-anilinophenyl)-2-hydroxyisobutyramide from which can be prepared an alpha, beta unsaturated aryl amide, such as N-(4-anilinophenyl)-methacrylamide.

BACKGROUND ART

Compounds such as N-(4-anilinophenyl)-methacrylamide have been prepared from methacryloyl chloride by methods as described in U.S. Pat. Nos. 3,658,769 and 3,852,350. Methacryoyl chloride is a severe lachrymator, relatively expensive, poisonous and highly corrosive.

Another process presently used for the production of alpha, beta unsaturated aryl amides is the ester process described in U.S. Pat. No. 3,907,893, which only gives maximum yields of 67 to 70%.

The synthesis of α, β unsaturated aryl amides is important since these compounds have been found to be effective polymerizable antioxidants.

In U.S. Pat. Nos. 3,907,893 and 3,852,350 the conversion of p-aminodiphenylamine is the limiting step. The p-amiondiphenylamine is the most costly reactant in the process, thus, an increase in the conversion would significantly lower the cost of the final product.

A great deal of effort has been expended in this area, however, the prior art does not suggest or disclose the process of the present invention wherein the product is produced via a dehydration of the α hydroxy isobutyramide of p-aminodiphenylamine.

There is a need for a process which does not involve the use of hazardous compounds such as methacryloyl chloride to produce methacrylamides.

The process of the present invention provides a method for preparing these amides and avoids the difficulties encountered in other preparations to date.

DISCLOSURE OF THE INVENTION

The process of the present invention comprises reacting (A) an organic acid having the following structural formula:

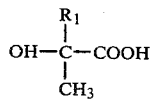

wherein $R_1$ is selected from the group consisting of hydrogen, methyl or phenyl radicals; with an aryl amine selected from one of the following structural formulae:

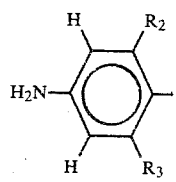 or 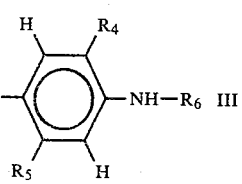

wherein $R_2$ and $R_3$ are the same or different alkyl radicals selected from the group consisting of isopropyl, secondary butyl, tert.-butyl, tert.-pentyl or tert.-hexyl; $R_4$ and $R_5$ are the same or different radicals selected from the group consisting of hydrogen, methyl or ethyl; and $R_6$ is selected from a phenyl radical or a alkyl substituted phenyl radical with one to three same or different alkyl substituents selected from either methyl or ethyl radicals; to produce a hydroxy aryl amide having one of the following structural formulae:

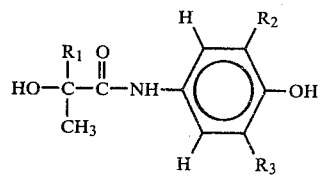

or

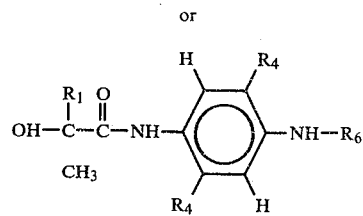

wherein $R_1$, $R_2$, $R_3$, $R_4$, $R_5$, and $R_6$ are defined as above, and (B) dehydrating the hydroxy aryl amide to form an α, β unsaturated amide having one of the following structural formulae:

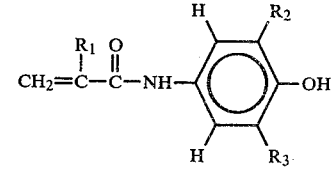

or

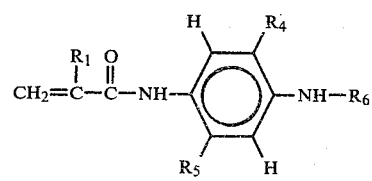

wherein $R_1$, $R_2$, $R_3$, $R_4$, $R_5$ and $R_6$ are defined as above.

Illustrative of the organic acids used in the process of this invention are alpha-hydroxy isobutyric acid, alpha-hydroxy propionic acid and 2-phenyl-2-hydroxy propionic acid.

Illustrative of the aryl amines used in the process of this invention are 4-aminodiphenylamine, 2-methyl-4-amino diphenylamine, 2,5-dimethyl-4-aminodiphenylamine, 2-ethyl-4-aminodiphenylamine, 2,6-di-tert.butyl-4-aminophenol, 2,6-di-isopropyl-4-aminophenol, 2,2'-dimethyl-4-aminodiphenylamine, and 4'-methyl-4-aminodiphenylamine.

Illustrative of the α, β unsaturated amides which are produced using the process of this invention are N-[4-(4-methylanilino)phenyl]methacrylamide, N-[4(2-methylanilino)-2-methylphenyl]methacrylamide, N-(4-anilinophenyl) methacrylamide, N-(4-anilinophenyl)acrylamide, N-(4-anilino-2-methylphenyl) methacrylamide, N-(3,5-di-tert.-butyl-4-hydroxyphenyl)methacrylamide, N-(3,5-di-isopropyl-4-hydroxyphenyl)acrylamide.

DETAILED DESCRIPTION OF THE INVENTION

The molar ratio of organic acid to aryl amine may vary widely, from between 10 to 1 to 1 to 10, however, a 5 to 1 to 1 to 5 molar ratio is preferred and the most preferred ratio is about an equal molar ratio.

Various dehydration methods known in the art may be applied to the dehydration of the hydroxy aryl amide. In general, most of the known methods of dehydration and reagents used are detailed in Houbenweyl: *Methoden der Organischen Chemie*, Ed. 4 Vol. 5, Pt. 1B, pages 45–104. These known methods may be applied in the present invention. One particularly good dehydration method involves the use of concentrated sulfuric acid as the dehydrating agent.

Using concentrated $H_2SO_4$ as the dehydrating agent at least a 1 to 1 molar ratio to the hydroxy aryl amide should be used with ratios at high as 1000 to 1 acceptable and ratios of between 5 to 1 and 50 to 1 being preferred.

Other methods of dehydration known to the art may be employed to dehydrate the hydroxy aryl amides in the process of this invention.

An inert organic solvent such as xylene, toluene, ethyl benzene, etc. may be used when reacting the organic acid with the aryl amine to prepare the hydroxy aryl amide. However, no solvent is necessary and no benefit is derived from their use, in fact, the reaction with a solvent present involves longer reaction times.

It is usually preferred that the water by-product of the reaction be distilled off from the neat melt of the organic acid and the aryl amine. By neat melt is meant that the reaction is conducted without the use of a solvent or diluent. However, an inert organic solvent such as xylene may be employed if better temperature control is desired.

A solvent may or may not be present in the dehydration step depending upon the nature of the dehydrating agent. (See Houbenweyl supra). For example, if concentrated $H_2SO_4$ is used as the dehydrating agent, it also serves as the solvent for the reaction.

The hydroxy aryl amide can be formed at any practical temperature. A normal reaction temperature is from 80° to 250° C. with the preferred temperature range being between 150° to 250° C. in the neat melt.

Temperatures of the dehydration step will depend upon the nature of the dehydrating agent. (See Houbenweyl supra). With concentrated $H_2SO_4$, the time, temperature and concentration are optimized to maximize the yield of the unsaturated amide and minimize the further reaction to hydrolyzed products. For example, a 10 percent hydroxy aryl amide/$H_2SO_4$ solution can be heated for 18 minutes at 98° to 100° C. to obtain 81 percent N-(4-anilinophenyl) methacrylamide. Those skilled in the art will readily be able to determine the temperature required for the particular dehydrating process being employed.

An inert atmosphere of nitrogen, argon, etc. is not necessary in preparing the hydroxy aryl amine, but if extremely elevated temperatures are employed an inert atmosphere may be desirable due to the oxygen sensitivity of the aromatic amines.

In the dehydration step, an inert atmosphere is not required, however, an inert atmosphere such as nitrogen, argon, etc. may be desirable due to the oxygen sensitivity of the (aromatic amines) products.

Concentrated sulfuric acid is used as the dehydration agent in the examples forthcoming, however, other well-known dehydrating agents such as N,N-dicyclohexylcarbodiimide may be used.

BEST MODE FOR CARRYING OUT THE INVENTION

EXAMPLE 1

Preparation of an Organic Acid

α-Hydroxy Isobutyric Acid

A one liter flask was charged with 193 milliliters (2.11 moles) of acetone cyanohydrin and 212 milliliters (2.12 moles) concentrated hydrochloric acid was placed in an addition funnel. The acid was slowly added dropwise to the stirred cyanohydrin. The temperature rose to approximately 100° C. before subsiding. A heating mantle was attached to maintain a temperature of 85°–98° C. during the addition of the remaining acid. After addition the temperature was maintained at 85°–98° C. for two hours. The mixture was cooled and the solid ammonium chloride by-product was filtered off, thoroughly washed with acetone and refiltered. The acetone extracts were combined with the initial filtrate and the solvent was extracted using reduced pressures. The residue was dissolved in ethyl ether and refiltered to remove any inorganic salt that remained. There was obtained 174 grams, 85% of theoretical yield of α-hydroxy isobutyric acid as a white crystalline solid.

EXAMPLE 2

Preparation of α-hydroxy aryl amide

N-(4-anilinophenyl)-2-hydroxy isobutyramide

With Solvent

A 500 milliliter resin pot was charged with 52 grams (0.05 moles) of α-hydroxy isobutyric acid from Example 1, 77.3 grams (0.42 moles) p-aminodiphenylamine, 1 gram p-toluene sulfonic acid and 140 mls. of xylene under a nitrogen blanket. A Dean-Stark water separator and a condenser was attached to the resin pot and the mixture was heated to vigorous reflux with $H_2O$ being removed as it was formed. After 3 hours of reflux the heat was removed and the product was allowed to crystallize in the resin pot under nitrogen. The product was broken up, washed with toluene, filtered and dried to obtain 104.4 grams (92% yield) of N-(4-anilinophenyl)-2-hydroxyisobutyramide with a melting point of 171°–174° C.

EXAMPLE 3

Preparation of α-hydroxy aryl amide

N-(4-anilinophenyl)-2-hydroxy-isobutyramide

No Solvent

A 100 milliliter flask was charged with 18.4 grams (0.10 mole) p-aminodiphenylamine and 10.6 grams (0.102 mole) α-hydroxy isobutyric acid from Example 1. The mixture was heated to 190° C. where dehydration of the amine-acid salt begins. Water was distilled from the mixture as the temperature slowly increased to 250° C. 2.35 milliliters of distillate was collected and the color of the mixture turned from blue-black to clear amber. After cooling the mixture to 190° C., the amber liquid was poured into a crystallizing dish whereupon it immediately crystallized to give 24.0 gram of N-(4-anilinophenyl)-2-hydroxy-isobutyramide (89% yield).

It should be noted that an acid catalyst, (p-toluene sulfonic acid in Example 2), is not used under the reaction conditions of Example 3, since the reaction temperatures are much higher than with the use of a solvent as in Example 2.

EXAMPLE 4

Dehydration Step

Preparation of N-(4-anilinophenyl)methacrylamide

H$_2$SO$_4$ as Solvent

In a large test tube was dissolved 10 grams (0.037 mole) of N-(4-anilinophenyl)-2-hydroxy-isobutyramide from Example 3 in 30 milliliters of concentrated H$_2$SO$_4$. The test tube was placed in a hot oil bath at 110° C. for three minutes. The reaction mixture was removed from the oil bath and slowly poured into a large excess of cold water. The product was filtered, washed with water and dried to yield 6 grams of product. NMR and elemental analysis showed that N-(4-anilinophenyl)methacrylamide was the product in 56.7% purity for a 36% yield of theory.

EXAMPLE 5

Dehydration Step

Preparation of N-(4-anilinophenyl)methacrylamide

H$_2$SO$_4$ as Solvent 4.85 Grams (0.018 moles) N-(4-anilinophenyl)-2-hydroxyisobutyramide from Example 3 was dissolved in 43.6 grams concentrated sulfuric acid at room temperature in a large test tube. The test tube was then placed in a boiling water bath for 18 minutes before being rapidly cooled in a stream of cold water. This reaction solution was then added dropwise to 800 milliliters of stirred cold water over a 45 minute period. The light green product was filtered off, washed with water and dried in the air to give 3.66 grams N-(4-anilinophenyl)methacrylamide (81% yield). Analysis showed a purity of 92.1%.

The product of Examples 4 and 5, N-(4-anilinophenyl)methacrylamide is a known anitioxidant capable of being polymerized in an emulsion free radical polymerization system. The copolymerizable antioxidants presently known in the art have several advantages over conventional antioxidants. The advantages of co-polymerized anitioxidants over conventional antioxidants are in roughly decreasing order of importance: nonextractability, nonvolatility, nondiscoloring properties and to some extent resistance to high temperature aging.

EXAMPLE 6

Polymerization of N-(4-anilinophenyl)methacrylamide in NBR

A sample of the product obtained from Example 5 was polymerized in NBR for comparison with N-(4-anilinophenyl) methacrylamide prepared by the acid chloride and ester processes of the prior art. N-(4-anilinophenyl methacrylamide from each process was copolymerized in a free radical polymerization with 67 parts of butadiene and 33 parts of acrylonitrile using cumene hyperoxide (CHP) as the initiator in the recipe set out below. The reaction was carried out at a temperature of 10° C. for 16 hours. Sodium dimethyldithio carbamate was used to shortstop the reaction.

| | |
|---|---|
| Butadiene | 67.00 |
| Acrylonitrile | 33.00 |
| Water | 190.00 |
| Soap | 2.50 |
| Na$_3$PO$_4$ | .20 |
| Versene Fe$_3$(in 5 cc .0173 NH$_2$SO$_4$) | .0568 |
| Fe$_2$SO$_4$ . 7H$_2$O | .0144 |
| Sodium formaldehyde sulfoxylate | .0412 |
| Tert. dodecyl mercaptan | .5 |
| Cumene hydroperoxide | .06 |
| N-(4-anilinophenyl)methacrylamide = A.M.A. | 1.80 |

Table I shows the percent of A.M.A. polymerized. Each A.M.A. sample was polymerized in duplicate. A.M.A. will hereinafter stand for the compound known as N-(4-anilinophenyl)methacrylamide.

TABLE I

Polymerization of A.M.A. in NBR

| | (Duplicate Runs) Polymerization | % Conversion | |
|---|---|---|---|
| A.M.A. Prepared By | Temp. °C. | 1st Run | 2nd Run |
| Dehydration Process (Example 5) | 10° | 83 | 87 |
| Acid Chloride Process | 10° | 88 | 88 |
| Ester Process | 10° | 80 | 92 |

Table I shows that the A.M.A. prepared by the process of this invention is comparable in polymerization activity to A.M.A. prepared by the known acid chloride and ester processes.

The duplicate polymerizations for each process were combined and then isopropyl alcohol coagulated. The polymer formed was extracted for 48 hours with hot methanol to remove any residual antioxidant, dried and dissolved in benzene. The benzene solution was allowed to evaporate in an aluminum tray and oxygen absorption measurements were made on the resulting polymer films. The testing procedure is described in *Industrial and Engineering Chemistry*, Vol. 43, Page 456 (1951). The results are given in Table II.

TABLE II

O$_2$ Absorption Test

| Polymer with A.M.A. from | Hours to 0.25% O$_2$ at 100° C. |
|---|---|
| Example 5 | 125 |
| Acid Chloride Process | 157 |
| Ester Process | 122 |

NBR without antioxidants will absorb 0.25% O$_2$ in less than 5 hours at 100° C. Table II shows that the A.M.A. prepared by process of this invention is comparable to the antioxidative activity of A.M.A. prepared by the prior art processes.

Dry extracted polymer for each process was submitted for analysis of percent of polymer bound antioxidant. Analysis showed that all three samples had 1% antioxidant present in the polymer.

This data clearly indicates that A.M.A. prepared by using the process of this invention has antioxidative properties equal to A.M.A. prepared using the prior art processes.

INDUSTRIAL APPLICABILITY

The process of the present invention provides a procedure for the synthesis of polymerizable antioxidant amides which is inexpensive and nonhazardous both to the environment and to employees.

While certain representative embodiments and details have been shown for the purpose of illustrating the invention, it will be apparent to those skilled in the art that various changes and modifications may be made herein without departing from the spirit or the scope of the invention.

I claim:

1. An improved process for the synthesis of a α,β unsaturated aryl amides comprising reacting an organic acid having general formula I:

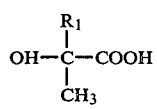

wherein $R_1$ is selected from the group consisting of hydrogen, methyl or phenyl radicals; with an aryl amine selected from one of the following structural formulae:

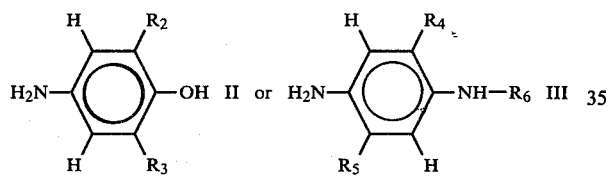

wherein $R_2$ and $R_3$ are the same or different alkyl radicals selected from the group consisting of isopropyl, secondary butyl, tert.-butyl, tert.-pentyl or tert.-hexyl; $R_4$ and $R_5$ are the same or different radicals selected from the group consisting of hydrogen, methyl or ethyl; and $R_6$ is selected from a phenyl radical or an alkyl substituted phenyl radical with one to three same or different alkyl substituents selected from either methyl or ethyl radicals; to produce a hydroxy aryl amide having one of the following structural formulae:

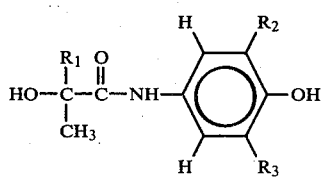

or

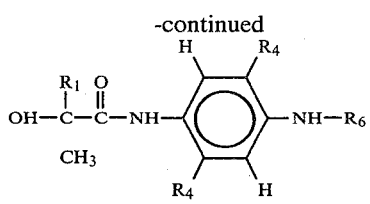

wherein $R_1$, $R_2$, $R_3$, $R_4$, $R_5$, and $R_6$ are defined as above, and (B) dehydrating, through use of concentrated sulfuric acid at a temperature of 98°–110° C. in at least a 1 to 1 molar ratio, the hydroxy aryl amide to form an α, β unsaturated amide having one of the following structural formulae:

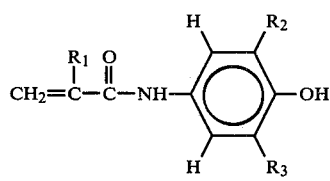

or

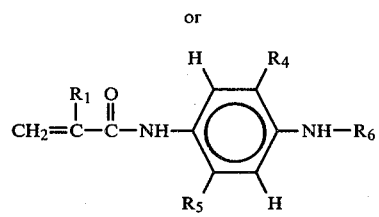

wherein $R_1$, $R_2$, $R_3$, $R_4$, $R_5$ and $R_6$ are defined as above.

2. A process as described in claim 1 above wherein the organic acid is select from the group consisting of α-hydroxy-isobutyric acid, α-hydroxy-propionic acid, and 2-phenyl-2-hydroxy-propionic acid.

3. A process as described in claim 1 wherein the aromatic amine is selected from the group consisting of 4-aminodiphenylamine, 2-methyl-4-aminodiphenylamine, 2,5-dimethyl-4-aminodiphenylamine, 2-ethyl-4-aminodiphenylamine, 2,6-di-tert.butyl-4-aminophenol, and 2,6-diisopropyl-4-aminophenol.

4. A process as described in claim 1 wherein the organic acid is selected from the group consisting of α-hydroxy-isobutyric acid, α-hydroxy-propionic acid, and 2-phenyl-2-hydroxy-propionic acid and the aromatic amine is selected from the group consisting of 4-aminodiphenylamine, 2-methyl-4-aminodiphenylamine, 2,5-dimethyl-4-aminodiphenylamine, 2-ethyl-4-aminodiphenylamine, 2,6-di-tert.butyl-4-aminophenol, and 2,6-diisopropyl-4-aminophenol.

5. A process described in claim 1 wherein the acid is α-hydroxy-isobutyric acid, the amine is 4-aminodiphenylamine and the reaction takes place in xylene solvent in the presence of an added acid catalyst.

6. A process in which 4-aminodiphenylamine and a 5% molar excess of α-hydroxy-isobutyric acid undergoes a condensation reaction at 150° to 250° C. without a solvent.

7. A process as described in claim 6 wherein the final product is dehydrated using concentrated sulfuric acid as the solvent and the dehydrating agent.

* * * * *

UNITED STATES PATENT OFFICE
CERTIFICATE OF CORRECTION

PATENT NO. : 4,286,105         Page 1 of 3
DATED : August 25, 1981
INVENTOR(S) : Dane K. Parker It is certified that error appears in the above-identified patent and that said Letters Patent are hereby corrected as shown below:

In column 2, structural formula V, delete

"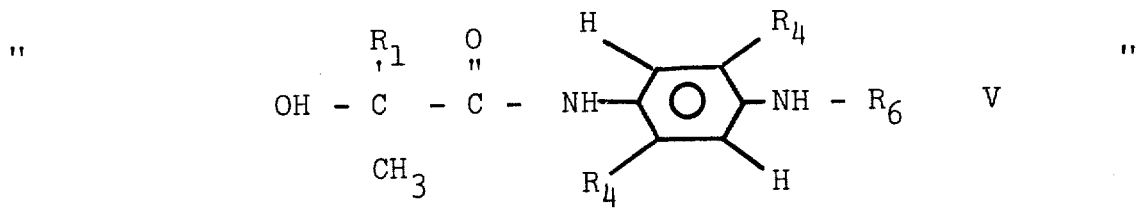"

and insert therefor

-- 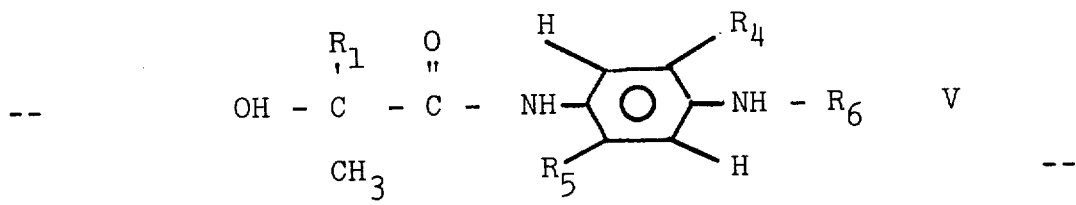 --

In column 5, line 67, delete "hyperoxide" and insert therefor -- hydroperoxide --.

UNITED STATES PATENT OFFICE
CERTIFICATE OF CORRECTION

PATENT NO. : 4,286,105　　　　　　　　　　　Page 2 of 3
DATED : August 25, 1981
INVENTOR(S) : Dane K. Parker It is certified that error appears in the above-identified patent and that said Letters Patent are hereby corrected as shown below:

In column 8, structural formula V, delete

"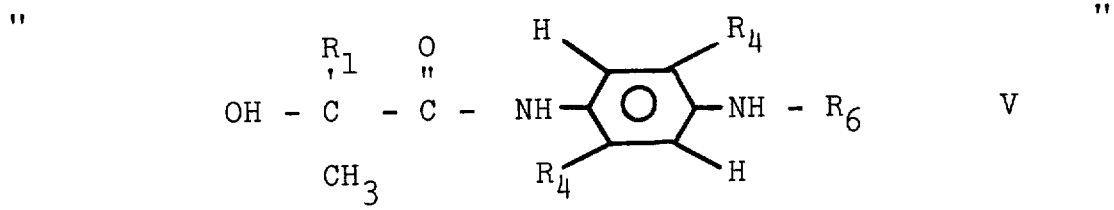"

and insert therefor

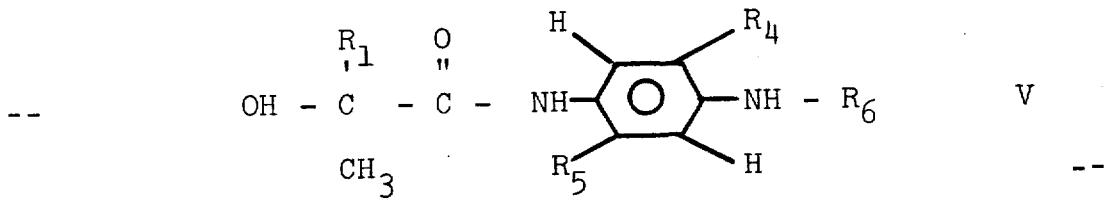

In column 8, line 36, delete "select" and insert therefor -- selected --.

UNITED STATES PATENT AND TRADEMARK OFFICE
CERTIFICATE OF CORRECTION

PATENT NO. : 4,286,105

DATED : August 25, 1981

INVENTOR(S) : Dane K. Parker

It is certified that error appears in the above-identified patent and that said Letters Patent is hereby corrected as shown below:

In column 8, line 54, after the word "process", insert

-- as --.

Signed and Sealed this

Third Day of July 1984

[SEAL]

Attest:

Attesting Officer

GERALD J. MOSSINGHOFF

Commissioner of Patents and Trademarks